(12) United States Patent
Jaffe et al.

(10) Patent No.: US 9,217,561 B2
(45) Date of Patent: Dec. 22, 2015

(54) SOLID STATE LIGHT SOURCE FOR PHOTOCURING

(71) Applicant: LUMENCOR, INC., Beaverton, OR (US)

(72) Inventors: Claudia B. Jaffe, Portland, OR (US); Steven M. Jaffe, Portland, OR (US); George S. Tylinski, Portland, OR (US)

(73) Assignee: LUMENCOR, INC., Beaverton, OR (US)

( * ) Notice: Subject to any disclaimer, the term of this patent is extended or adjusted under 35 U.S.C. 154(b) by 270 days.

(21) Appl. No.: 13/901,727

(22) Filed: May 24, 2013

(65) Prior Publication Data

US 2013/0335992 A1    Dec. 19, 2013

Related U.S. Application Data

(60) Provisional application No. 61/660,386, filed on Jun. 15, 2012.

(51) Int. Cl.
| | |
|---|---|
| A61B 1/06 | (2006.01) |
| F21V 29/00 | (2015.01) |
| F21V 11/00 | (2015.01) |
| F21V 8/00 | (2006.01) |
| G02B 27/10 | (2006.01) |

(Continued)

(52) U.S. Cl.
CPC .............. *F21V 29/004* (2013.01); *A61C 19/003* (2013.01); *F21V 11/00* (2013.01); *G02B 6/0008* (2013.01); *G02B 27/10* (2013.01); *G02B 27/141* (2013.01); *G02B 6/3849* (2013.01); *G02B 6/4292* (2013.01); *G02B 2006/4297* (2013.01)

(58) Field of Classification Search
CPC .............. A61B 19/004; A61B 19/003; A61N 2005/0652; F21W 2131/202
USPC ................. 362/231, 572, 573; 433/29; 607/88
See application file for complete search history.

(56) References Cited

U.S. PATENT DOCUMENTS

| 1,998,054 A | 4/1935 | McBurney |
|---|---|---|
| 3,313,337 A | 4/1967 | Bernat |

(Continued)

FOREIGN PATENT DOCUMENTS

| CA | 2 280 398 | 4/2000 |
|---|---|---|
| EP | 1 426 807 | 12/2003 |

(Continued)

OTHER PUBLICATIONS

International Search Report dated Dec. 31, 2008, Application No. PCT/US2008/072394, 10 pages.

(Continued)

*Primary Examiner* — Peggy Neils
(74) *Attorney, Agent, or Firm* — Tucker Ellis LLP

(57) ABSTRACT

A compact passively-cooled solid state illumination system is provided as a replacement for conventional arc light, metal halide and Xenon white-light sources for photocuring applications. The solid state illumination system utilizes LED modules to generate high intensity light output suitable for photocuring. The light output is continuous in the visible spectrum from 380 nm to 530 nm and is suitable for photocuring using a wide range of photoinitiators. A touchscreen interface allows programming of spectral output, intensity and duration. Output can be initiated using the touchscreen interface and/or a foot pedal.

14 Claims, 9 Drawing Sheets

(51) Int. Cl.
   *A61C 13/15*   (2006.01)
   *G02B 27/14*   (2006.01)
   *G02B 6/38*    (2006.01)
   *G02B 6/42*    (2006.01)

(56) References Cited

U.S. PATENT DOCUMENTS

| | | | |
|---|---|---|---|
| 3,637,285 A | 1/1972 | Stewart | |
| 3,759,604 A | 9/1973 | Thelen | |
| 3,881,800 A | 5/1975 | Friesem | |
| 3,982,151 A | 9/1976 | Ludovici | |
| 4,003,080 A | 1/1977 | Maiman | |
| 4,298,820 A | 11/1981 | Bongers | |
| 4,371,897 A | 2/1983 | Kramer | |
| 4,510,555 A | 4/1985 | Mori | |
| 4,539,687 A | 9/1985 | Gordon | |
| 4,602,281 A | 7/1986 | Nagasaki et al. | |
| 4,626,068 A | 12/1986 | Caldwell | |
| 4,642,695 A | 2/1987 | Iwasaki | |
| 4,644,141 A | 2/1987 | Hagen | |
| 4,657,013 A | 4/1987 | Hoerenz et al. | |
| 4,695,332 A | 9/1987 | Gordon | |
| 4,695,732 A | 9/1987 | Ward | |
| 4,695,762 A | 9/1987 | Berkstresser | |
| 4,713,577 A | 12/1987 | Gualtieri | |
| 4,724,356 A | 2/1988 | Daehler | |
| 4,798,994 A | 1/1989 | Rijpers | |
| 4,804,850 A | 2/1989 | Norrish et al. | |
| 4,852,985 A | 8/1989 | Fujihara et al. | |
| 4,937,661 A | 6/1990 | Van der Voort | |
| 4,995,043 A | 2/1991 | Kuwata | |
| 5,052,016 A | 9/1991 | Mahbobzadeh | |
| 5,089,860 A | 2/1992 | Deppe | |
| 5,109,463 A | 4/1992 | Lee | |
| 5,126,626 A | 6/1992 | Iwasaki | |
| 5,128,846 A | 7/1992 | Mills et al. | |
| 5,137,598 A | 8/1992 | Thomas | |
| 5,193,015 A | 3/1993 | Shanks | |
| 5,200,861 A | 4/1993 | Moskovich | |
| 5,226,053 A | 7/1993 | Cho | |
| 5,231,533 A | 7/1993 | Gonokami | |
| 5,233,372 A | 8/1993 | Matsumoto | |
| 5,249,195 A | 9/1993 | Feldman | |
| 5,285,131 A | 2/1994 | Muller | |
| 5,289,018 A | 2/1994 | Okuda | |
| 5,312,535 A | 5/1994 | Waska | |
| 5,315,128 A | 5/1994 | Hunt | |
| 5,332,892 A | 7/1994 | Li et al. | |
| 5,345,333 A | 9/1994 | Greenberg | |
| 5,363,398 A | 11/1994 | Glass | |
| 5,416,342 A | 5/1995 | Edmond et al. | |
| 5,416,617 A | 5/1995 | Loiseaux | |
| 5,418,584 A | 5/1995 | Larson | |
| 5,428,476 A | 6/1995 | Jensen | |
| 5,469,018 A | 11/1995 | Jacobsen | |
| 5,475,281 A | 12/1995 | Heijboer | |
| 5,478,658 A | 12/1995 | Dodabalapur | |
| 5,489,771 A | 2/1996 | Beach et al. | |
| 5,493,177 A | 2/1996 | Muller | |
| 5,500,569 A | 3/1996 | Blomberg | |
| 5,542,016 A | 7/1996 | Kaschke | |
| 5,616,986 A | 4/1997 | Jacobsen | |
| 5,634,711 A * | 6/1997 | Kennedy et al. | 362/119 |
| 5,644,676 A | 7/1997 | Blomberg | |
| 5,658,976 A | 8/1997 | Carpenter | |
| 5,669,692 A | 9/1997 | Thorgersen | |
| 5,671,050 A | 9/1997 | De Groot | |
| 5,674,698 A | 10/1997 | Zarling | |
| 5,690,417 A | 11/1997 | Polidor et al. | |
| 5,715,083 A | 2/1998 | Takayama | |
| 5,719,391 A | 2/1998 | Kain | |
| 5,757,014 A | 5/1998 | Bruno | |
| 5,781,338 A | 7/1998 | Kapitza et al. | |
| 5,803,579 A | 9/1998 | Turnbull et al. | |
| 5,804,919 A | 9/1998 | Jacobsen | |
| 5,808,759 A | 9/1998 | Okamori et al. | |
| 5,827,438 A | 10/1998 | Blomberg | |
| 5,833,827 A | 11/1998 | Anazawa | |
| 5,858,562 A | 1/1999 | Utsugi | |
| 5,864,426 A | 1/1999 | Songer | |
| 5,942,319 A | 8/1999 | Oyama | |
| 5,955,839 A | 9/1999 | Jaffe | |
| 5,984,861 A | 11/1999 | Crowley | |
| 6,089,740 A * | 7/2000 | Forehand et al. | 362/573 |
| 6,110,106 A | 8/2000 | MacKinnon et al. | |
| 6,154,282 A | 11/2000 | Lilge | |
| 6,198,211 B1 | 3/2001 | Jaffe | |
| 6,200,134 B1 * | 3/2001 | Kovac et al. | 433/29 |
| 6,204,971 B1 | 3/2001 | Morris | |
| 6,222,673 B1 | 4/2001 | Austin | |
| 6,293,911 B1 | 9/2001 | Imaizumi et al. | |
| 6,299,338 B1 | 10/2001 | Levinson | |
| 6,304,584 B1 | 10/2001 | Krupke | |
| 6,366,383 B1 | 4/2002 | Roeder | |
| 6,392,341 B2 | 5/2002 | Jacobsen | |
| 6,404,127 B2 | 6/2002 | Jacobsen | |
| 6,404,495 B1 | 6/2002 | Melman | |
| 6,422,994 B1 | 7/2002 | Kaneko et al. | |
| 6,444,476 B1 | 9/2002 | Morgan | |
| 6,513,962 B1 | 2/2003 | Mayshack et al. | |
| 6,517,213 B1 | 2/2003 | Fujita et al. | |
| 6,529,322 B1 | 3/2003 | Jones | |
| 6,542,231 B1 | 4/2003 | Garrett | |
| 6,544,734 B1 | 4/2003 | Briscoe | |
| 6,594,075 B1 | 7/2003 | Kanao et al. | |
| 6,608,332 B2 | 8/2003 | Shimizu | |
| 6,614,161 B1 | 9/2003 | Jacobsen | |
| 6,614,179 B1 | 9/2003 | Shimizu et al. | |
| 6,637,905 B1 | 10/2003 | Ng | |
| 6,642,652 B2 | 11/2003 | Collins | |
| 6,649,432 B1 | 11/2003 | Eilers | |
| 6,674,575 B1 | 1/2004 | Tandler et al. | |
| 6,680,569 B2 | 1/2004 | Mueller-Mach et al. | |
| 6,685,341 B2 | 2/2004 | Ouderkirk et al. | |
| 6,690,467 B1 | 2/2004 | Reel | |
| 6,717,353 B1 | 4/2004 | Mueller | |
| 6,747,710 B2 | 6/2004 | Hall | |
| 6,791,259 B1 | 9/2004 | Stokes et al. | |
| 6,791,629 B2 | 9/2004 | Moskovich | |
| 6,795,239 B2 | 9/2004 | Tandler et al. | |
| 6,843,590 B2 | 1/2005 | Jones | |
| 6,869,206 B2 | 3/2005 | Zimmerman et al. | |
| 6,870,165 B2 | 3/2005 | Amirkhanian | |
| 6,926,848 B2 | 8/2005 | Le Mercier | |
| 6,958,245 B2 | 10/2005 | Seul et al. | |
| 6,960,872 B2 | 11/2005 | Beeson et al. | |
| 6,981,970 B2 | 1/2006 | Karni | |
| 6,991,358 B2 | 1/2006 | Kokogawa | |
| 6,995,355 B2 | 2/2006 | Rains, Jr. et al. | |
| 7,009,211 B2 | 3/2006 | Eilers | |
| 7,011,421 B2 | 3/2006 | Hulse et al. | |
| 7,035,017 B2 | 4/2006 | Tadic-Galeb | |
| 7,083,610 B1 | 8/2006 | Murray et al. | |
| 7,141,801 B2 | 11/2006 | Goodwin | |
| 7,153,015 B2 | 12/2006 | Brukilacchio | |
| 7,192,161 B1 | 3/2007 | Cleaver et al. | |
| 7,205,048 B2 | 4/2007 | Naasani | |
| 7,208,007 B2 | 4/2007 | Nightingale et al. | |
| 7,211,833 B2 | 5/2007 | Slater, Jr. et al. | |
| 7,239,449 B2 | 7/2007 | Leitel et al. | |
| 7,283,230 B2 * | 10/2007 | Ostler et al. | 356/317 |
| 7,300,175 B2 | 11/2007 | Brukilacchio | |
| 7,316,497 B2 | 1/2008 | Rutherford et al. | |
| 7,384,797 B1 | 6/2008 | Blair | |
| 7,416,313 B2 | 8/2008 | Westphal et al. | |
| 7,422,356 B2 | 9/2008 | Hama et al. | |
| 7,427,146 B2 | 9/2008 | Conner | |
| 7,445,340 B2 | 11/2008 | Conner | |
| 7,467,885 B2 | 12/2008 | Grotsch et al. | |
| 7,488,088 B2 | 2/2009 | Brukilacchio | |
| 7,488,101 B2 | 2/2009 | Brukilacchio | |
| 7,498,734 B2 | 3/2009 | Suehiro et al. | |
| 7,540,616 B2 | 6/2009 | Conner | |
| 7,595,513 B2 | 9/2009 | Plank et al. | |

(56) References Cited

U.S. PATENT DOCUMENTS

| | | | |
|---|---|---|---|
| 7,633,093 B2 | 12/2009 | Blonder et al. | |
| 7,709,811 B2 | 5/2010 | Conner | |
| 7,746,560 B2 | 6/2010 | Yamazaki | |
| 7,802,910 B2* | 9/2010 | Middlemass et al. | 362/573 |
| 7,832,878 B2 | 11/2010 | Brukilacchio | |
| 7,837,348 B2 | 11/2010 | Narendran et al. | |
| 7,846,391 B2 | 12/2010 | Jaffe et al. | |
| 7,854,514 B2 | 12/2010 | Conner | |
| 7,857,457 B2 | 12/2010 | Rutherford et al. | |
| 7,898,665 B2 | 3/2011 | Brukilacchio et al. | |
| 7,922,346 B2* | 4/2011 | Katsuda et al. | 362/5 |
| 7,976,307 B2 | 7/2011 | Plank et al. | |
| 8,029,142 B2 | 10/2011 | Conner | |
| 8,098,375 B2 | 1/2012 | Brukilacchio | |
| 8,231,383 B2* | 7/2012 | Gill et al. | 433/29 |
| 8,242,462 B2 | 8/2012 | Jaffe et al. | |
| 8,258,487 B1 | 9/2012 | Jaffe et al. | |
| 8,263,949 B2 | 9/2012 | Jaffe et al. | |
| 8,279,442 B2 | 10/2012 | Brukilacchio et al. | |
| 8,309,940 B2 | 11/2012 | Jaffe et al. | |
| 8,389,957 B2 | 3/2013 | Jaffe et al. | |
| 8,466,436 B2 | 6/2013 | Jaffe et al. | |
| 8,493,564 B2 | 7/2013 | Brukilacchio et al. | |
| 8,992,042 B2* | 3/2015 | Eichenholz | 362/231 |
| 2001/0038992 A1* | 11/2001 | Otsuka | 433/29 |
| 2001/0055208 A1 | 12/2001 | Kimura | |
| 2002/0109844 A1 | 8/2002 | Christel et al. | |
| 2002/0127224 A1 | 9/2002 | Chen | |
| 2003/0007087 A1 | 1/2003 | Hakamata et al. | |
| 2003/0044160 A1 | 3/2003 | Jonese et al. | |
| 2003/0095401 A1 | 5/2003 | Hanson et al. | |
| 2003/0127609 A1 | 7/2003 | El-Hage et al. | |
| 2003/0160151 A1 | 8/2003 | Zarate et al. | |
| 2003/0230728 A1 | 12/2003 | Dai | |
| 2003/0233138 A1 | 12/2003 | Spooner | |
| 2004/0090600 A1 | 5/2004 | Blei | |
| 2004/0090794 A1* | 5/2004 | Ollett et al. | 362/555 |
| 2004/0247861 A1 | 12/2004 | Naasani | |
| 2004/0264185 A1 | 12/2004 | Grotsch et al. | |
| 2005/0062404 A1 | 3/2005 | Jones et al. | |
| 2005/0116635 A1 | 6/2005 | Walson et al. | |
| 2005/0146652 A1 | 7/2005 | Yokoyama et al. | |
| 2005/0152029 A1 | 7/2005 | Endo | |
| 2005/0184651 A1 | 8/2005 | Cheng | |
| 2005/0201899 A1 | 9/2005 | Weisbuch | |
| 2005/0248839 A1 | 11/2005 | Yamaguchi | |
| 2005/0260676 A1 | 11/2005 | Chandler | |
| 2005/0263679 A1 | 12/2005 | Fan | |
| 2006/0002131 A1 | 1/2006 | Schultz et al. | |
| 2006/0030026 A1 | 2/2006 | Garcia | |
| 2006/0060872 A1 | 3/2006 | Edmond et al. | |
| 2006/0060879 A1 | 3/2006 | Edmond | |
| 2006/0114960 A1 | 6/2006 | Snee | |
| 2006/0170931 A1 | 8/2006 | Guo | |
| 2006/0237658 A1 | 10/2006 | Waluszko | |
| 2006/0282137 A1 | 12/2006 | Nightingale et al. | |
| 2007/0009210 A1 | 1/2007 | Hulse | |
| 2007/0053184 A1 | 3/2007 | Brukilacchio | |
| 2007/0053200 A1 | 3/2007 | Brukilacchio | |
| 2007/0058389 A1 | 3/2007 | Brukilacchio | |
| 2007/0064202 A1 | 3/2007 | Moffat et al. | |
| 2007/0086006 A1 | 4/2007 | Ebersole et al. | |
| 2007/0126017 A1 | 6/2007 | Krames et al. | |
| 2007/0211460 A1 | 9/2007 | Ravkin | |
| 2007/0253733 A1 | 11/2007 | Fey | |
| 2007/0262731 A1 | 11/2007 | Jaffar et al. | |
| 2007/0279914 A1 | 12/2007 | Rutherford et al. | |
| 2007/0279915 A1 | 12/2007 | Rutherford et al. | |
| 2007/0280622 A1 | 12/2007 | Rutherford et al. | |
| 2007/0281322 A1 | 12/2007 | Jaffe et al. | |
| 2007/0284513 A1 | 12/2007 | Fan | |
| 2007/0297049 A1 | 12/2007 | Schadwinkel et al. | |
| 2008/0079910 A1 | 4/2008 | Rutherford et al. | |
| 2008/0224024 A1 | 9/2008 | Ashdown | |
| 2008/0291446 A1 | 11/2008 | Smith | |
| 2009/0122533 A1 | 5/2009 | Brukilacchio | |
| 2009/0196046 A1 | 8/2009 | Rutherford et al. | |
| 2009/0268461 A1 | 10/2009 | Deak et al. | |
| 2010/0188017 A1 | 7/2010 | Brukilacchio | |
| 2011/0044858 A1 | 2/2011 | Jaffe et al. | |
| 2012/0106192 A1 | 5/2012 | Brukilacchio | |
| 2012/0181936 A1 | 7/2012 | Jaffe et al. | |
| 2012/0181937 A1 | 7/2012 | Jaffe et al. | |
| 2012/0238472 A1 | 9/2012 | Jaffe et al. | |
| 2012/0252704 A1 | 10/2012 | Jaffe et al. | |
| 2012/0307514 A1 | 12/2012 | Brukilacchio et al. | |
| 2013/0052607 A1* | 2/2013 | Gersh et al. | 433/27 |
| 2013/0099135 A1 | 4/2013 | Jaffe et al. | |
| 2013/0188331 A1 | 7/2013 | Jaffe et al. | |
| 2013/0188383 A1 | 7/2013 | Jaffe et al. | |
| 2013/0188384 A1 | 7/2013 | Jaffe et al. | |
| 2013/0188388 A1 | 7/2013 | Jaffe et al. | |

FOREIGN PATENT DOCUMENTS

| | | |
|---|---|---|
| GB | 0943756 | 12/1963 |
| GB | 2 000 173 A | 1/1979 |
| JP | 02-804873 | 7/1998 |
| JP | 2005-195485 | 7/2005 |
| JP | 2005-243973 | 9/2005 |
| JP | 2006-049814 | 2/2006 |
| JP | 2007-133435 | 5/2007 |
| JP | 2008139796 | 6/2008 |
| KR | 20-1999-0041018 | 12/1999 |
| KR | 10-2006-0055934 | 5/2006 |
| KR | 10-2006-089104 | 8/2006 |
| WO | WO 02/080577 | 10/2002 |
| WO | WO 2004/114053 | 12/2004 |
| WO | WO 2006/067885 | 6/2006 |
| WO | WO 2006/120586 | 11/2006 |

OTHER PUBLICATIONS

International Search Report for PCT/US2010021843 dated Aug. 19, 2010, 9 pages.

Extended European Search Report for PCT/US2008072394 dated Oct. 7, 2011, 9 pages.

International Search Report dated Jun. 19, 2012 for Application No. PCT/US2011/063030, 11 pages.

Extended European Search Report for PCT/US2007/069490 dated Oct. 26, 2012, 8 pages.

International Search Report dated Jun. 3, 2013 for Application No. PCT/US2013/029931, 11 pages.

Albrecht, M., et al., "Scintillators and Wavelength Shifters for the Detection of Ionizing Radiation," Astroparticle, Particle and Space Physics, Detectors and Medical Physics Applications, ICATPP-8, M. Barone, et al., Eds, World Scientific, pp. 502-511 (2004).

Da-Lite Screen Company, Inc., www.da-lite.com, 46 pages website downloads as of Oct. 8, 1998.

DDS™ Rear Projection Screens, LORS™ Reflection Screens, ©1998 Physical Optics Corporation, Torrance, CA, 2 pages.

Deck, L., et al., "Two color light-emitting-diode source for high precision phase-shifting interferometry", Optics Letters, vol. 18, No. 22, Nov. 15, 1993, pp. 1899-1901.

Depp, S.W., et al., "Flat Panel Displays," Scientific American, pp. 90-97, Mar. 1993.

Flor-Henry, M., et al., "Use of a Highly Sensitive Two-Dimensional Luminescence Imaging System to Monitor Endogenous Bioluminescence in Plant Leaves," BMC Plant Biology, vol. 4, No. 19, Nov. 2004.

Hamberg, I. and Granqvist, C.G., "Evaporated Sn-doped $In_2O_3$ films: Basic optical properties and applications to energy-efficient windows," Journal of Applied Physics, vol. 60, No. 11, pp. R123-R159, Dec. 1, 1986.

Handbook of Optics, vol. 1—Fundamentals, Techniques, and Design, Second Edition, Chapter 42: Optical Properties of Films and Coatings, J.A. Dobrowolski, pp. 42.3-42.25, McGraw-Hill, Inc., © 1995.

Haroche, S., et al., "Cavity Quantum Electrodynamics," Scientific American, pp. 54-62, Apr. 1993.

(56) References Cited

OTHER PUBLICATIONS

Hecht, Jeff, "Diverse fiberoptic systems require varied sources," Laser Focus World, vol. 36, No. 1, pp. 155-161, Jan. 2000.

Hemingway, D.J. and Lissberger, P.H., "Effective Refractive Indices of Metal-Dielectric Interference Filters," Applied Optics, vol. 6, No. 3, pp. 471-476, Mar. 1967.

Hinds, E.A., "Spectroscopy of Atoms in a Micron-Sized Cavity," (date and periodical title unknown), pp. 18-19.

Holloway, R.J. and Lissberger, P.H., "The Design and Preparation of Induced Transmission Filters," Applied Optics, vol. 8, No. 3, pp. 653-660, Mar. 1969.

Huo, D.T.C., et al., "Reticulated Single-Crystal Luminescent Screen," J. Electrochem. Soc., vol. 133, No. 7, pp. 1492-1497, Jul. 1986.

Jenmar Visual Systems, Sunnyvale, CA, 4 pages, no date, but at least as early as Oct. 15, 1998.

Landau, B.V. and Lissberger, P.H., "Theory of Induced-Transmission Filters in Terms of the Concept of Equivalent Layers," Journal of the Optical Society of America, vol. 62, No. 11, pp. 1258-1264, Nov. 1972.

Launer, Herbert F., "Exposure Meter for Precision Light Dosage", The Review of Scientific Instruments, vol. 20, No. 2, Feb. 1949, pp. 103-109.

Lissberger, P.H., "Coatings with Induced Transmission," Applied Optics, vol. 20, No. 1, pp. 95-103, Jan. 1, 1981.

Mauch, R.H., et al., "Optical Behaviour of Electroluminescent Devices," Springer Proceedings in Physics, vol. 38, Electroluminescence, © Springer-Verlag Berlin, Heidelberg, pp. 291-295 (1989).

Morgan, C. G., et al., "New Approaches to Lifetime-Resolved Luminescence Imaging", Journal of Fluorescence, vol. 7, No. 1, 1997, pp. 65-73.

Pelletier, E. and Macleod, H.A., "Interference Filters with Multiple Peaks," Journal of the Optical Society of America, vol. 72, No. 6, pp. 683-687, Jun. 1982.

Plasma Display Manufacturers of the American Display Consortium, "Recommended Research Topics on Plasma Display for the DARPA Sponsored Phosphor Center of Excellence," pp. 1-2, Mar. 24, 1993.

Poelman, D., et al., "Spectral Shifts in Thin Film Electroluminescent Devices: An Interference Effect," J. Phys. D: Appl. Phys., vol. 25, pp. 1010-1013 (1992).

Schott Glass Technologies, Inc., Schott Total Customer Care, Contrast Enhancement Filters, Duryea, PA, 6 pages, Jan. 1998.

Schubert, E.F., et al., "Giant Enhancement of Luminescence Intensity in Er-doped $Si/SiO_2$ Resonant Cavities," Appl. Phys. Lett. vol. 61, No. 12, pp. 1381-1383, Sep. 21, 1992.

Stewart Filmscreen Corporation®, www,stewartfilm.com, 34 pages website downloads as of Oct. 8, 1998.

Tuenge, R.T., "Current Status of Color TFEL Phosphors," Electroluminescence—Proceedings of the Sixth International Workshop on Electroluminescence, El Paso, Tex., pp. 173-177, May 1992.

Vlasenko, N.A., et al., "Interference of Luminescent Emission from an Evaporated Phosphor," Opt. Spect., vol. 11, pp. 216-219 (1961).

Vlasenko, N.A., et al., "Investigation of Interference Effects in Thin Electroluminescent ZnS—Mn Films," Opt. Spect., vol. 28, pp. 68-71 (1970).

Whitaker, Jerry C., "Electronic Displays: Technology, Design, and Applications," McGraw-Hill, Inc., pp. 185-192 (1994).

World Watch, Photonics Spectra, "IR Reflective Coating Boosts Bulb's Output, Recycling of IR Energy Saves Power, Cuts Costs" pp. 40-41, Jan. 1991.

Yamamoto, Y., et al., "Optical Processes in Microcavities," Physics Today, pp. 66-73, Jun. 1993.

Yokoyama, H., "Physics and Device Applications of Optical Microcavities," Science, vol. 256, pp. 66-70, Apr. 3, 1992.

Young, L., "Multilayer Interference Filters with Narrow Stop Bands," Applied Optics, vol. 6, No. 2, pp. 297-312, Feb. 1967.

International Search Report dated Sep. 4, 2013 for Application No. .PCT/US2013/043134, 11 pages.

\* cited by examiner

FIG. 1A
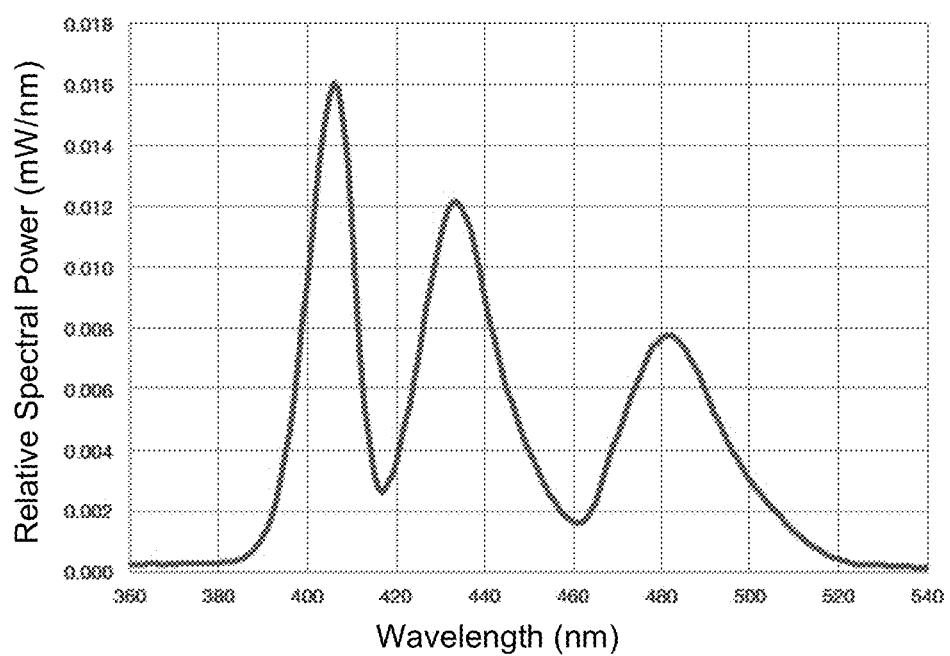
FIG. 1B

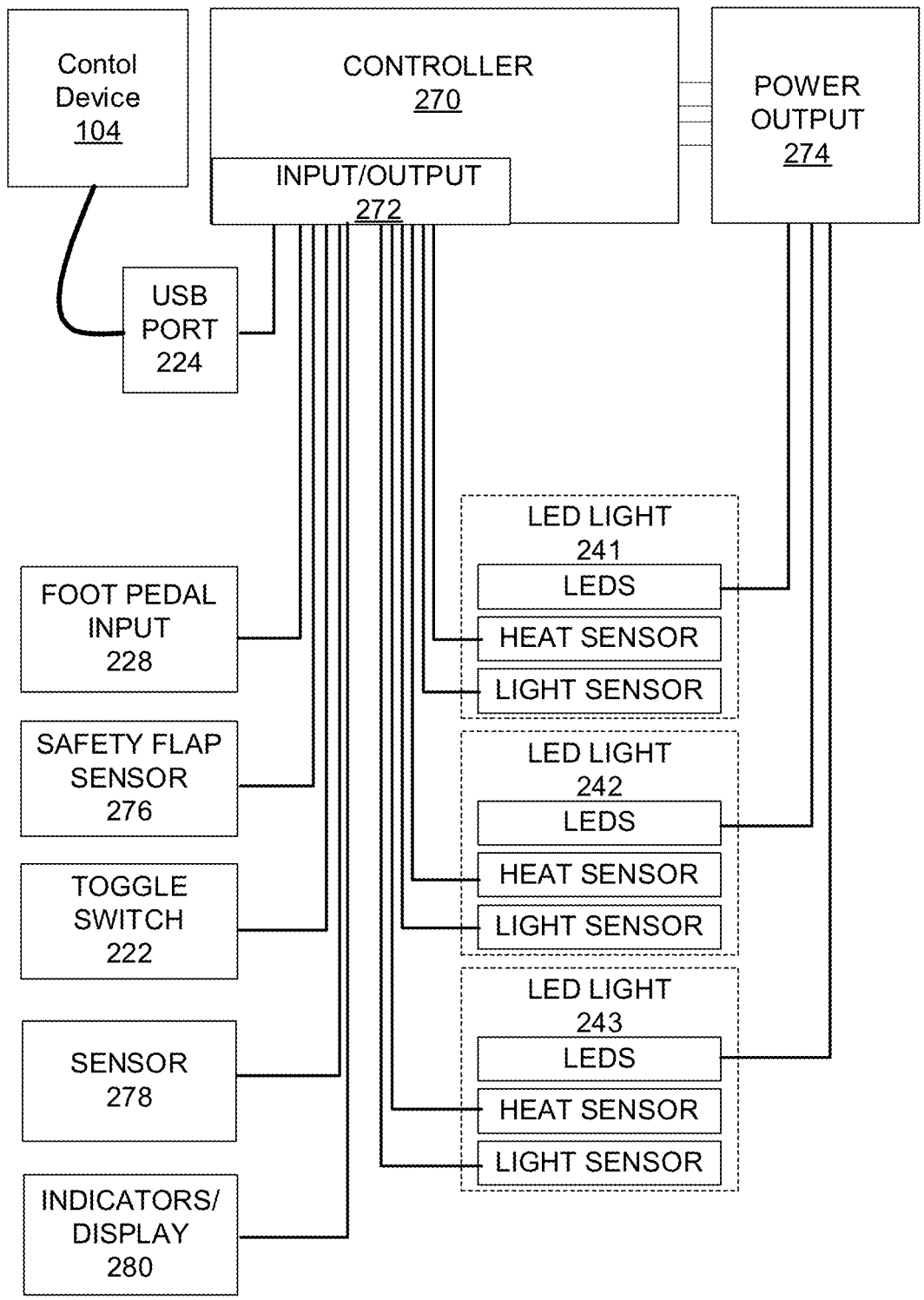

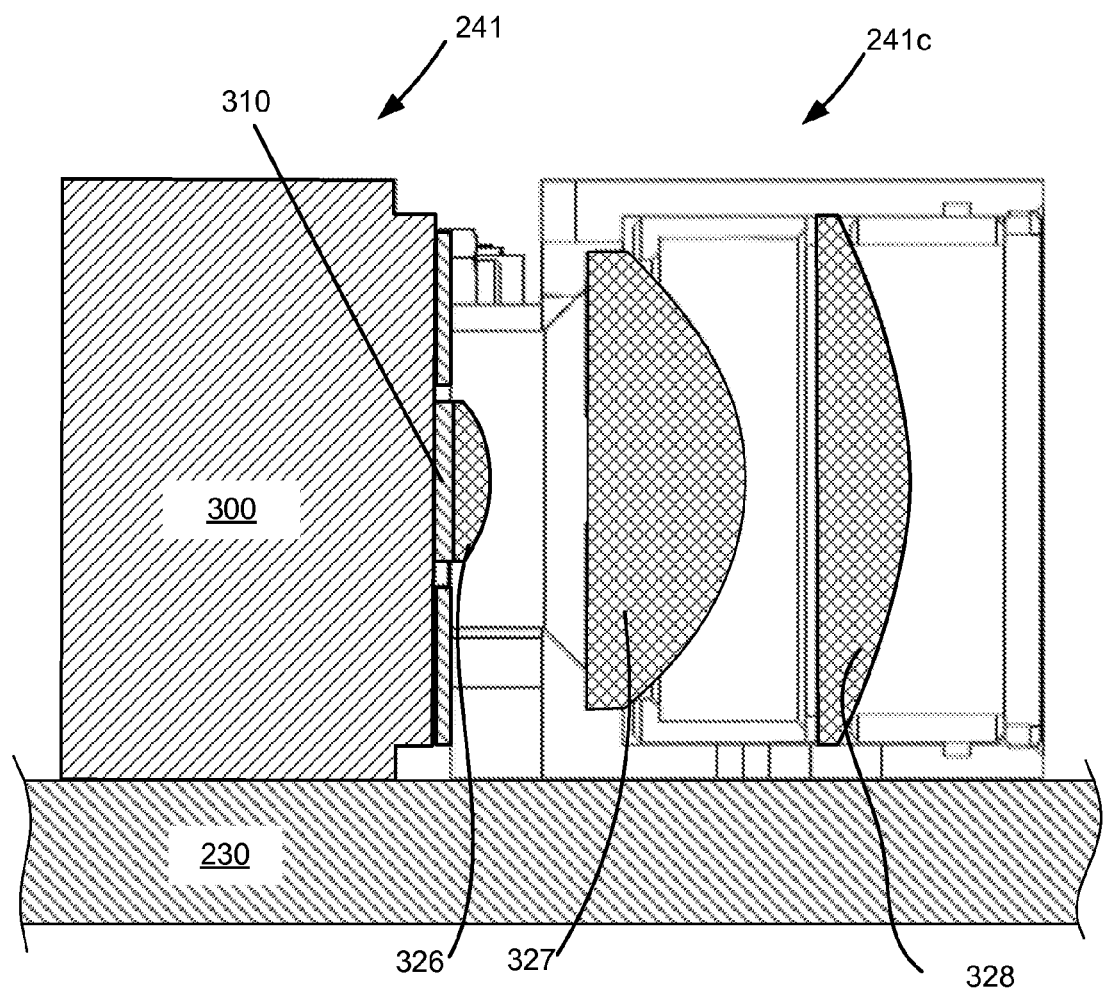

FIG. 4A
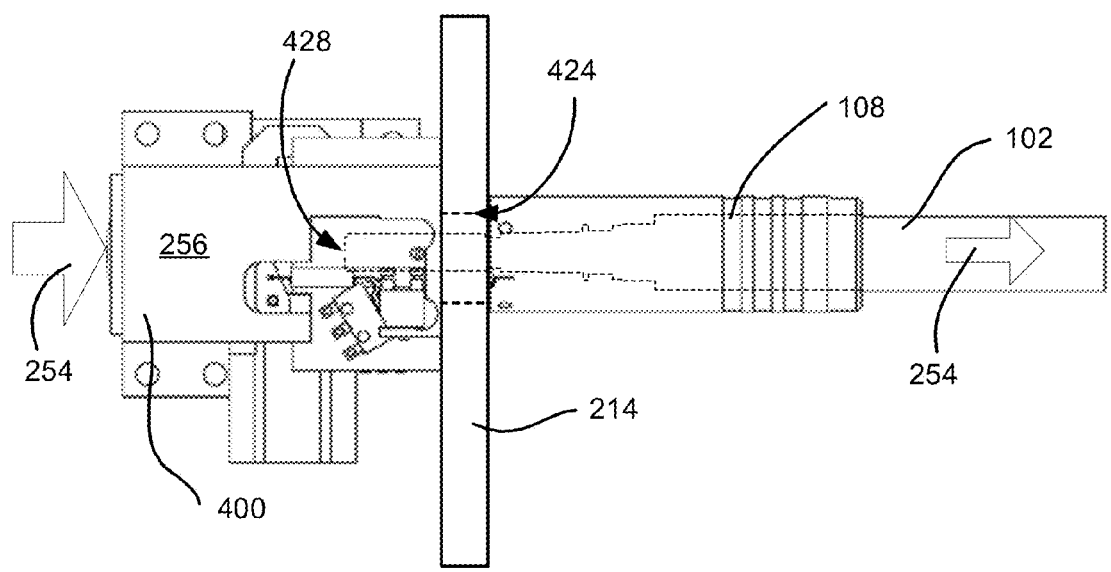
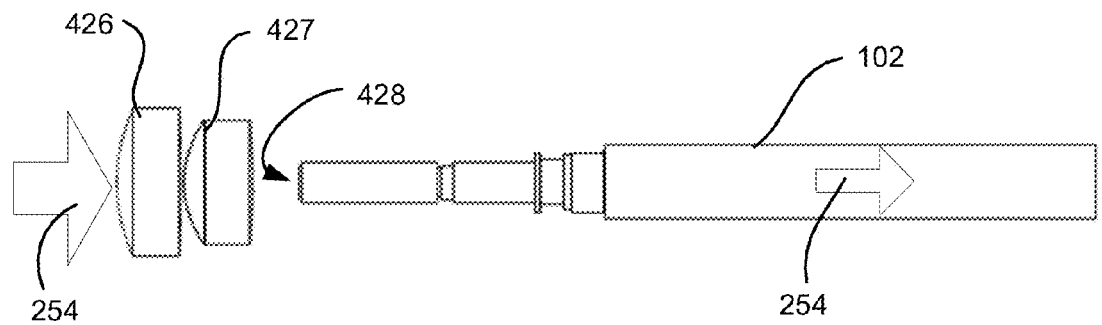
FIG. 4B

SOLID STATE LIGHT SOURCE FOR PHOTOCURING

CLAIM OF PRIORITY

The present application claims priority to U.S. Provisional Patent Application entitled "Solid State Light Source For Photocuring" Application No. 61/660,386, filed on Jun. 15, 2012 which application is incorporated herein by reference.

RELATED APPLICATIONS

The present application is related to the following patents and patent applications which are incorporated herein by reference in their entireties:

U.S. Pat. No. 7,846,391, granted Dec. 7, 2010, entitled "Bioanalytical Instrumentation Using A Light Source Subsystem," U.S. Publication No. 2007/0281322 filed May 21, 2007;

U.S. Pat. No. 7,709,811, granted May 4, 2010 entitled "Light Emitting Diode Illumination System," U.S. Publication No. 2009/0008573 filed Jul. 2, 2008;

U.S. Pat. No. 8,098,375, granted Jan. 17, 2012 entitled "Light Emitting Diode Illumination System," U.S. Publication No. 2009/0040523 filed Aug. 5, 2008;

U.S. patent application Ser. No. 13/012,658, filed Jan. 24, 2011 entitled "Light Emitting Diode Illumination System," U.S. Publication No. 2011/0116261; and U.S. patent application Ser. No. 12/691,601, now U.S. Pat. No. 8,242,462, granted Aug. 14, 2012, entitled "Lighting Design of High Quality Biomedical Devices," U.S. Publication No. 2010/0187440 filed Jan. 21, 2010.

FIELD OF THE INVENTION

The present invention relates to systems for providing light to induce curing, hardening, and/or polymerization of monomeric, oligomeric or polymeric materials. Photocuring applications include, by way of example only, dentistry, coatings, imaging, inks, manufacturing, plastic, electronics, and packaging.

BACKGROUND OF THE INVENTION

Photocuring systems have been developed in which visible and/or ultraviolet light is used to induce curing, hardening, and/or polymerization of monomeric, oligomeric or polymeric materials. Generally speaking, a photocurable resin/adhesive includes a photoinitiator responsible for initiating free-radical polymerization of the resin. The resin remains in a liquid/workable condition until polymerization is initiated. In order to initiate polymerization, light source is used to provide light of a wavelength suitable for absorption by the photo initiator. The photoinitiator enters an excited state upon absorption of photons of the correct wavelength inducing the creation of free-radicals. The free-radicals induce curing, hardening, and/or polymerization of monomeric, oligomeric or polymeric resin/adhesive.

Light energy is typically provided by one of four types of curing lights: quartz-tungsten-halogen (QTH), arc lamps, light-emitting diode (LED), arc lamps, and argon laser. Both QTH and arc lamps have broad emission spectra suitable for initiating polymerization in a broad range of resins. However, QTH and arc lamps also emit a great deal of heat/infrared. The heat/infrared output is reduced utilizing filters which may also be used to select output wavelengths suitable for particular photoinitiators. The large heat output however requires the QTH and arc lamp systems to have substantial thermal management systems and also reduces the life span of the lamps such that costly replacement parts are required. Moreover, both QTH and arc lamps have significant warm-up periods before spectral output is stable. Thus, in practice the lamps must be kept running continuously while light output is controlled using a shutter. This further reduces the effective lifespan of the lights.

Argon laser systems can be used to provide light for photocuring applications. The light output is coherent and can thus be used to generate high intensity illumination with photons of a selected wavelength. However, the emission spectra of the Argon laser is very narrow and may not be compatible with some photocurable resins. Moreover, Argon laser systems are expensive and have significant thermal regulation requirements LEDs (light-emitting diodes) have matured significantly within the last decades. LEDs emit light in specific wavelengths and generate much less heat relative to arc and QTH lamps thereby providing for longer lifespan, easy switching, consistent output and lower power consumption. However LEDs presents trade-offs with respect to emission wavelength dependent intensity, broad emission spectrum (spectral half width on the order of 30 nm or more), poor spectral stability, and the wide angular range of emission. The narrow band emission may not be compatible with some photocurable resins. In addition, the process used to manufacture LED's cannot tightly control their spectral stability; anyone wishing to use LED's in applications requiring a good spectral stability typically works directly with a supplier to essentially hand-pick the LED's for the particular application. Moreover the spectral output of an LED varies with temperature. Also, LED's emit light over a wide angular range (50% of light intensity emitted at) 70°). While optics can narrow the emission band and focus the light output, the resulting loss in power and increase in thermal output further complicates the use of LEDs for photocuring. Thus, it can be difficult to provide sufficient light at a wavelength suitable for exciting a particular photoinitiator.

While lighting manufacturers cannot provide all things to all applications, it is precisely this breadth of demand for which a light engine can be designed. To that end, products are not simple sources, but rather light engines, sources and all the ancillary components required to provide pure, powerful, light to the sample or as close to it as mechanically possible. A qualitative comparison of light engine performance as a function of source technology is summarized in Table I.

TABLE I

A qualitative comparison of light source technology.

| Source Technology | Useable Light | Uniformity | Temporal Response | Heat Generation | Durability | Cost |
|---|---|---|---|---|---|---|
| Arc Lamp | med | poor | none | high | low | high |
| Laser | high | poor | none | low | low | very high |

TABLE I-continued

A qualitative comparison of light source technology.

| Source Technology | Useable Light | Uniformity | Temporal Response | Heat Generation | Durability | Cost |
|---|---|---|---|---|---|---|
| LED | low | poor | fast | low | high | medium |
| QTH | low | poor | none | medium | low | medium |
| LED | high | high | fast | low | high | low |

A wide range of photoinitiators are available. To initiate polymerization it is essential to provide sufficient light energy at a wavelength which can be absorbed by a selected photoinitiator. However, each photoinitiator has a particular absorption spectra. Additionally, the light energy may have to pass through the resin and other materials in order to reach the photoinitiator. Resins incorporating a photoinitiator can affect transmission and absorption of light in different ways. Accordingly, it may be difficult to ensure sufficient light energy is provided at a wavelength suitable for exciting the photoinitiator. Without proper absorption, free radical polymerization may not occur uniformly throughout the resin. Moreover, where narrow band light sources, such as LEDs, are used the wavelength provided will not be suitable for exciting all photoinitiators in all compositions and manufacturing environments.

Accordingly it would be desirable to provide an LED light source for photocuring that overcomes limitations of the prior art.

SUMMARY OF THE INVENTION

The present invention provides an LED light engine system suitable for photocuring. The LED light engine system is a compact, passively cooled, durable, inexpensive solid state lighting solution, uniquely well suited to the production of light for photocuring. In an embodiment of the invention, this light engine can provide powerful, stable, inexpensive light across a range of wavelengths suitable for photocuring. The LED light engine system is designed to directly replace the entire configuration of light management components with a single, simple unit. Power, spectral breadth and purity, stability and reliability data demonstrates the advantages of the LED light engine system for photocuring applications. Performance and cost analyses are superior to traditional optical subsystems based on QTH, arc lamps, and lasers. Moreover the LED light engine has relatively small footprint, and low heat output such that it has lower power requirements and no need for moving parts—such as a fan.

In an embodiment, the present invention provides a compact passively-cooled solid state illumination system usable as a replacement for conventional arc light, metal halide and Xenon white-light sources for photocuring applications. The solid state illumination system utilizes LED modules to generate high intensity light output suitable for photocuring. The light output is continuous in the visible spectrum from 380 nm to 530 nm and is suitable for photocuring using a wide range of photoinitiators. A touchscreen interface allows programming of spectral output, intensity and duration. Output can be initiated using the touchscreen interface and/or a foot pedal.

Embodiments of the present invention are directed to an LED light engine system suitable for use as a replacement for conventional QTH and arc light photocuring lamps. In particular embodiments, the LED light engine generates a broad band of wavelengths between 380 nm and 530 nm suitable for exciting a wide range of photoinitiators.

Another embodiment of the present invention relates to an improved system for cooling the LED modules of the LED light engine system which reduces contamination of the LED modules and optical pathway from cooling airflow. The system includes means for conductive transmission of heat away from LED modules to a remote heat sink which is passively cooled.

Other objects and advantages of the present invention will become apparent to those skilled in the art from the following description of the various embodiments, when read in light of the accompanying drawings.

BRIEF DESCRIPTION OF THE FIGURES

Various embodiments of the present invention can be described in detail based on the following figures.

FIG. 1A shows a view of an LED light engine system according to an embodiment of the present invention.

FIG. 1B shows the spectral power output of the LED light engine system of FIG. 1A.

FIG. 2G illustrates a control system of the LED Light Engine of FIGS. 2A & 2B.

FIG. 3C shows a sectional view of the LED module of FIG. 3A.

FIG. 4A shows a top view of an output optics subsystem of the LED Light Engine of FIGS. 2A & 2B according to an embodiment of the invention.

FIG. 4B shows a top view of the optical components of the output optics subsystem of FIG. 4A.

Figure 2A:
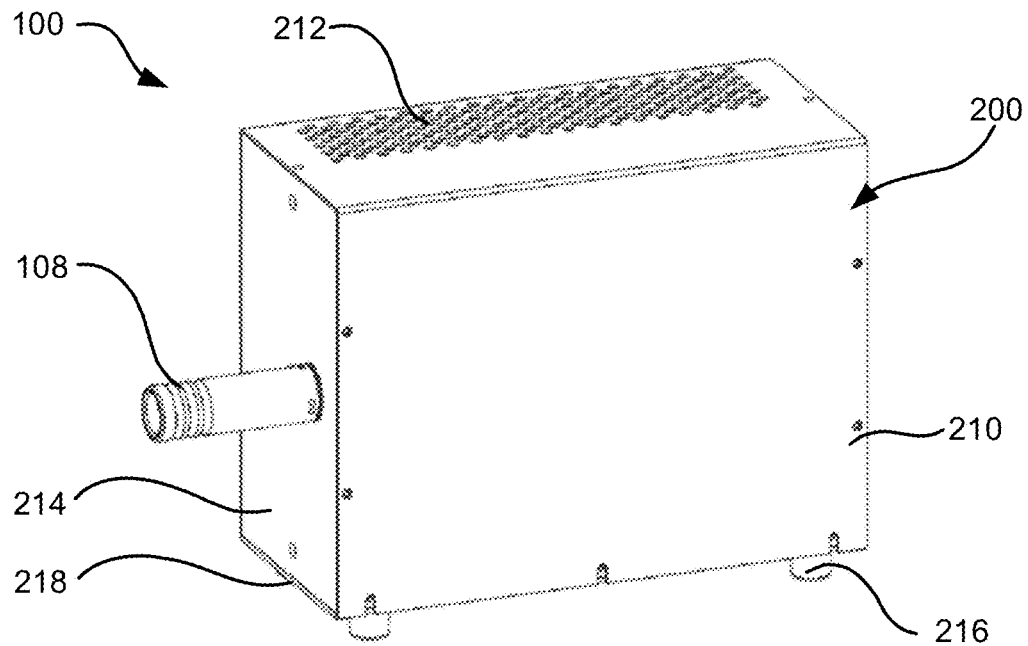
FIGS. 2A and 2B show exterior views of LED Light Engine according to an embodiment of the invention.

In the figures common reference numerals are used to indicate like elements throughout the drawings and detailed description; therefore, reference numerals used in a drawing may or may not be referenced in the detailed description specific to such drawing if the associated element is described elsewhere. The first digit in a three digit reference numeral indicates the series of figures in which the referenced item first appears. Likewise the first two digits in a four digit reference numeral.

DETAILED DESCRIPTION OF THE INVENTION

LED Light Engine System for Photocuring

While no one lighting solution can best satisfy all instrument architectures, an LED light engine according to an embodiment of the invention combines the best of solid state technologies to meet or outperform the traditional technologies listed in Table I on the basis of all figures of merit across all wavelengths desired for photocuring. In an embodiment of the invention, an LED light engine can emit light exceeding 500 mW/color with intensifies up to 10 W/cm² at wavelength suitable for photocuring. The present invention offers a smart alternative for light generation. The capabilities of the LED light engine are highlighted in Table II. The high performance illumination provided by the LED light engine is embodied in a single compact unit designed to replace the entire ensemble of lighting components. The sources, excitation filters, multicolor switching capabilities and fast pulsing are contained within one box with a small footprint such that no external optics or mechanics are required.

TABLE II

Led Light Engine Metrics.

Key Metrics:

| | |
|---|---|
| Spectral Output | Three selected wavelengths suitable for photocuring >_ 100 mW/spectral band 1-10 W/cm |
| Peak Wavelength | Optimal for different floors, adjustable bandwidths |
| Power Stability | >99% over 24 hours |
| Spectral Width | 10 to 50 nm |
| Spectral Drift | <1% in 24 hours |
| Color Dependence | None |
| Lifetime | >5000 hrs |
| Footprint | Amenable to portability |
| Maintenance | None, no consumable components for the light engine's lifetime |

In various embodiments of the present invention, an LED light engine includes LED modules having light emitting diodes which emit wavelengths of light, which suitable for exciting a range of photoinitiators. The LEDs operate through the process of spontaneous emission, which results in a much larger selection of available wavelengths than is available for efficient stimulated emission (laser action). The outputs of LED modules each including LEDs which emit one or more color of light are combined using optics into a single output to produce multiple colors simultaneously or in sequence. The LED modules can be illuminated continuously, can be controlled in intensity, and can be pulsed on and off rapidly as necessary or desired to excite the photoinitiator in a particular application. The LED modules can be switched off between uses to eliminate the heat output. This can be contrasted with alternatives such as QTH lamps, arc lamps, and lasers which are unstable unless they are operated continuously.

Because of the solid state nature and independently operable designs of the LED modules, coupled to fast (approximately 10 ns) decay times of typical materials employed, an LED light engine outperforms any broad spectrum source in terms of support for switching control. QTH and arc lamp based sources are coupled to filters and/or shutters with mechanical supports that relegate them to 1 to 50 millisecond regimes and require continuous operation of the lamp. The LED light engine incorporates all that capability into its highly integrated design. Therefore switching times are limited today by the electronics of the boards controlling the sources. Rise times of less than 20 μs and fall times of less than 2 μs are can be achieved. Moreover each color can be switched independently and is compatible with triggering by TTL, RS232 and USB and intensity control by RS232, USB or manually.

Using an LED light engine, effectively instantaneous excitation of photoinitiators can be performed to achieve desired curing effects with no external hardware beyond the light engine itself. Moreover, because the LED light engine is based on solid state technologies, they are extremely stable both in short duration experiments and over long term use. The LED light engine is powered by 24 V power supplies operated in DC mode, therefore there is no 60 Hz noise. All colors perform similarly. In 24 hours of continuous operation, the output fluctuates on the order of 1%. Short term stability on the order of 1.0 ms is approximately 0.5%. Short term stability for 0.1 ms is diminished by a factor of ten to 0.05%.

FIG. 1A shows a view of an LED light engine system 110 according to an embodiment of the present invention. As shown in FIG. 1A, LED light engine system 110 includes, LED light engine 100, light guide 102, control device 104, a foot pedal (not shown) is also provided with LED light engine system 110. LED light engine 100 includes LED modules for each discrete output based on solid state technologies tailored to best satisfy that output requirement complete with collection and delivery optics. Light guide 102, receives the light output from the LED light engine 100 and transmits it to the location and/or equipment where the light is to be used for Photocuring. Light guide 102, may be, for example, a liquid light guide or fiber optic light guide. Light guide 102, connects to an adapter 108 on the exterior of LED light engine 100. Control device 104, is in this embodiment a touchscreen tablet running software which allows the control device 104 to control operation of LED light engine 100. The touchscreen tablet, enables the user to set intensity, a countdown timer and even program custom curing cycles. Initiation of such programmed outputs can be actuated by the touchscreen or a foot-pedal (not shown). Control device 104 is connected to LED light engine 100 by USB cable 106, however, in alternative embodiments, a wireless or network connection can be used (Bluetooth, Wifi, NFC, Ethernet etc).

LED light engine 100 has a compact and novel fan-free design. The use of solid state light sources in combination with optimized thermal management allow for cool operation without the use of fans. LED light engine 100 has a long lifetime and is ideal for durable, reproducible, robust curing. A dual interlock system prevents light output from LED light engine 100 both mechanically and electronically when the light guide 102 is removed. The LED light engine 100 has no replaceable parts and no maintenance. Instant warm-up time and superior stability result in highly reproducible optical output power. LED light engine 100 is capable of fast on/off times that can be precisely controlled as well as intensity control. In an embodiment, LED light engine system 110 has the features shown Table III.

TABLE III

Photocuring LED Light Engine System Features.

| | |
|---|---|
| Source | Multiple solid state sources operating simultaneously |
| Wavelength Range | 380-530 nm (see FIG. 1A). |
| Power Intensity | 13 W/cm2 with a 3 mm diameter liquid light guide |
| Switching Speed | 5 kHz with turn on/off ~10 μs |
| Light Delivery | 3 or 5 mm diameter light guide adapter (LLG sold separately) |
| Easy to install | Pre-aligned, simple to operate, no maintenance |
| Lifetime | ~20,000 hours, 18 month warranty to end user |
| Safety Features | Dual electronic and mechanical safety interlock system |
| Interface | 7-inch, 1280 × 600 resolution touchscreen LCD control pad |
| Power requirements | 41 W, 24 V DC, 1.7 A power supply. |
| Dimensions (W × L × H) | 110 mm × 230 mm × 190 mm (4.2 in × 9.1 in × 7.5 in) |
| Weight | 3.6 kg (~8 lbs) |
| Shipment Contents | LED Light Engine, DC Power Supply, Touchscreen Control Pad, USB cable, foot pedal and cable, 3 mm diameter light guide adapter, Power supply for Touchscreen Control Pad. |

FIG. 1B shows the spectral power output of the LED light engine system 110 of FIG. 1A. As illustrated by FIG. 1B, and LED light engine system 110 is powerful, intense and produces a broad spectral light output over the range of wavelengths from 380 nm to 530 nm light, suitable for activating common photoinitiators. LED light engine 100 provides an output well matched for photocuring adhesives designed for UVA and visible wavelength curing. LED light engine system 110 is a high-performance device which generates nearly one watt of optical output power.

As shown in FIG. 1B, LED light engine system 110 produces high intensity visible light across a broad range of wavelengths suitable for photocuring LEDs (light-emitting diodes). The system exhibits good spectral stability, and focused emission. The wide emission band is compatible with most photocurable resins. Temperature is well controlled to maintain both lifespan and spectral stability. Thus, sufficient light is provided at wavelengths suitable for exciting particular photoinitiators. Moreover, the visible light generated by LED light engine system 110 has better penetration into photocurable resins than UV light, and the wide emission band means that the photoinitiator can be excited reliably across a wide range of compositions, environments, depths of resin etc thereby ensuring reliable and effective photocuring.

LED Light Engine For Photocuring

Figure 2B:
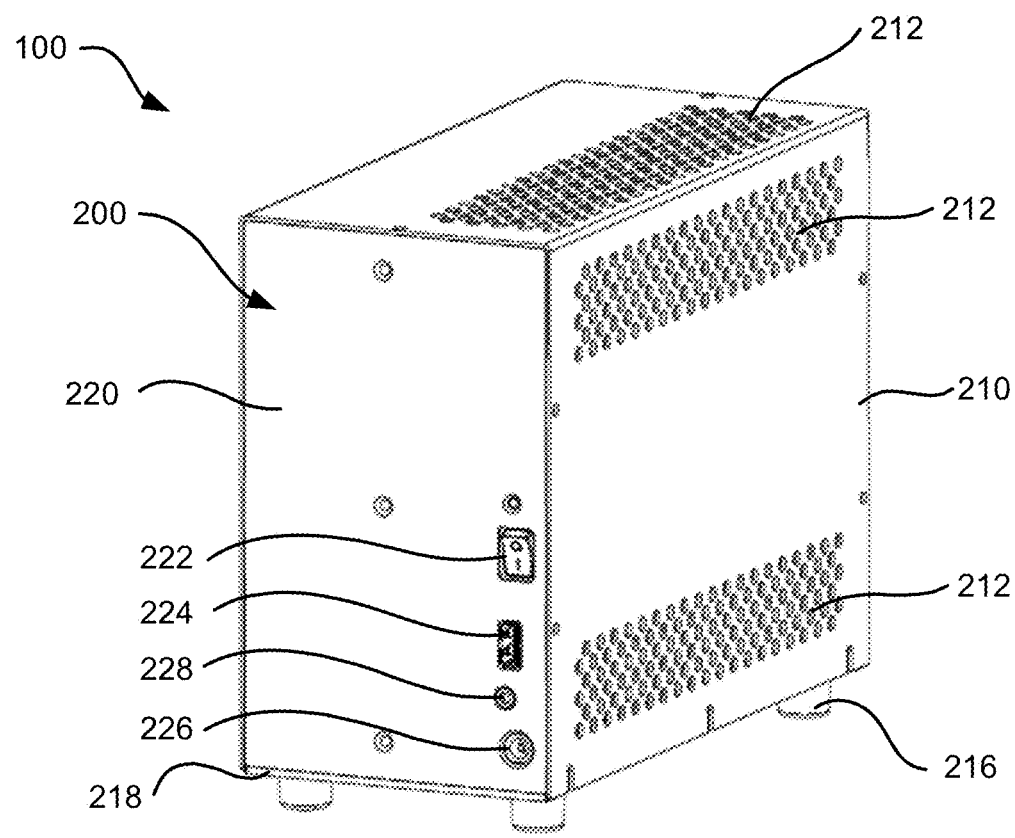
Figure 2C:
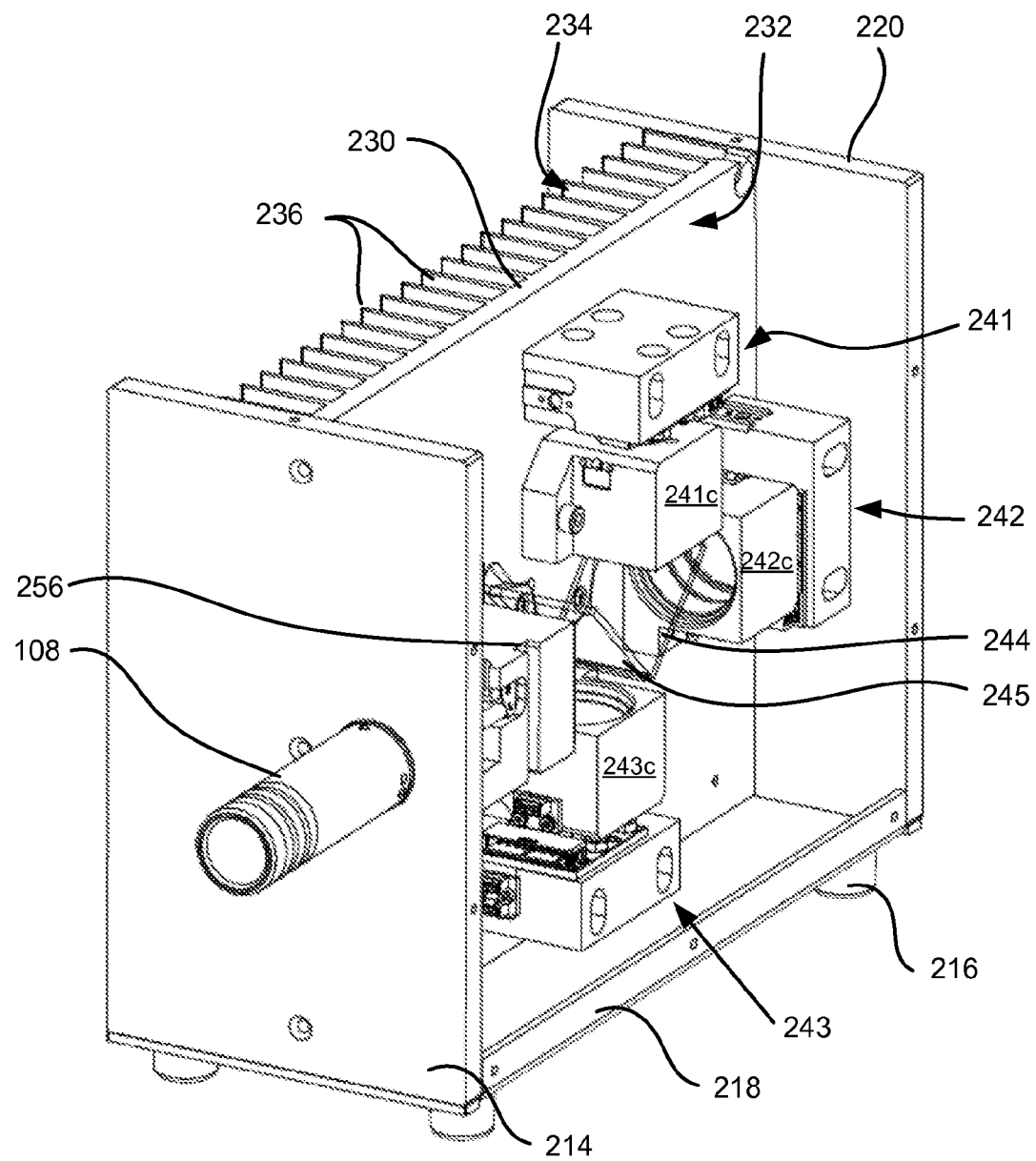
FIG. 2C shows a perspective internal view of the LED Light Engine of FIGS. 2A & 2B.
Figure 2D:
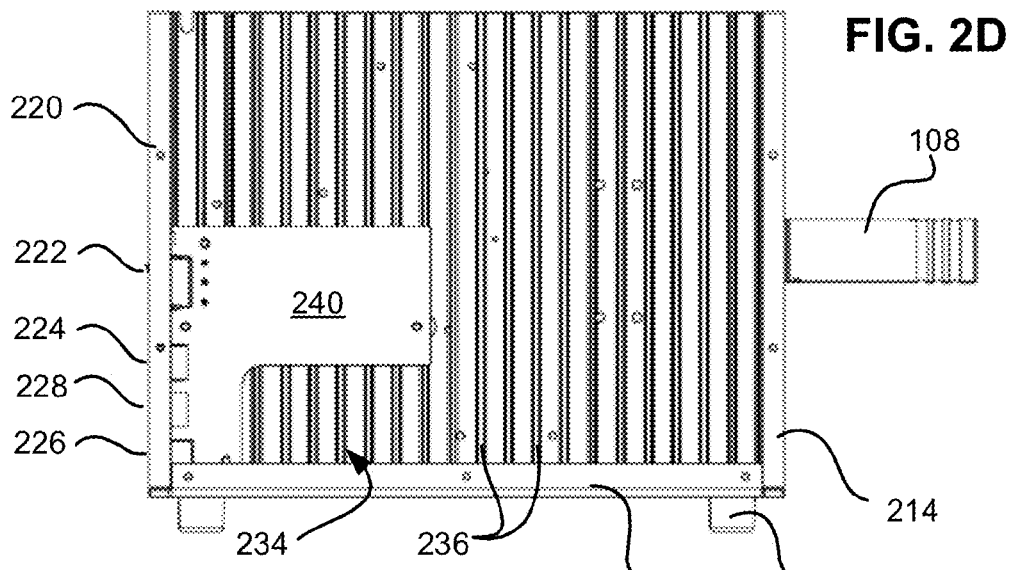
FIGS. 2D and 2E show side internal views of the LED Light Engine of FIGS. 2A & 2B.
Figure 2E:
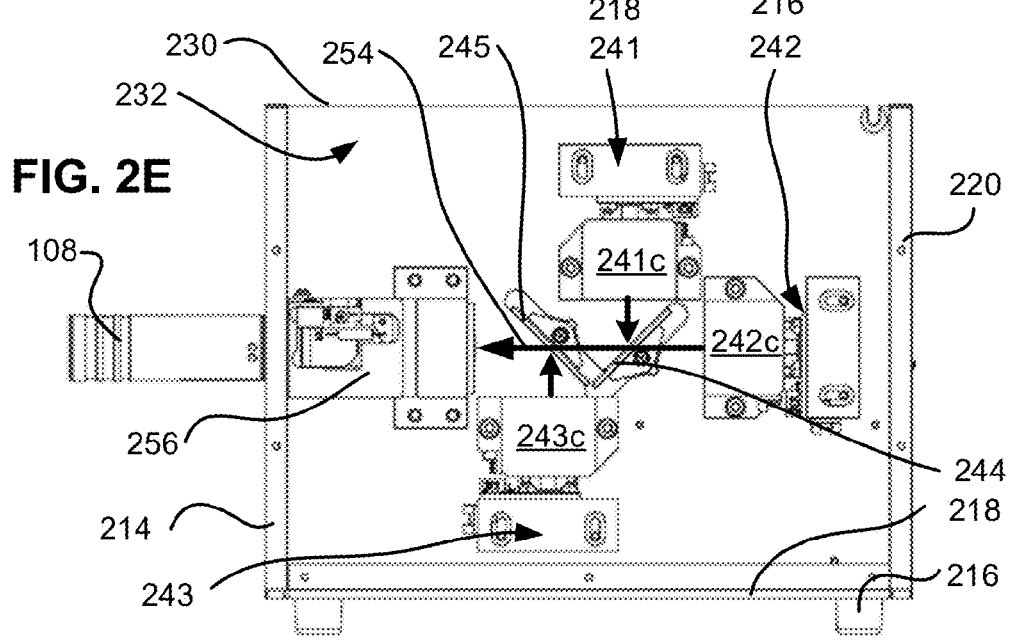
Figure 2F:
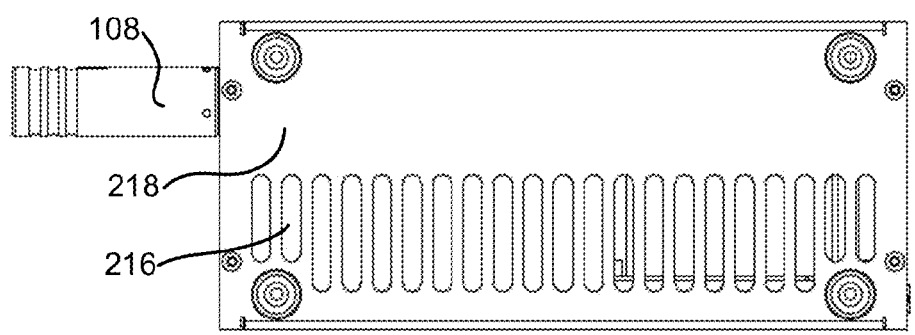
FIG. 2F shows a bottom view of the LED Light Engine of FIGS. 2A & 2B.

FIGS. 2A-2G show views of LED light engine 100 of the LED light engine system 110 FIG. 1A. FIGS. 2A and 2B show exterior views of LED light engine 100. FIG. 2C shows a perspective view of LED light engine 100 with the cover removed. FIGS. 2D and 2E show side views of LED light engine 100 with the cover removed. FIG. 2F shows a bottom view of LED light engine 100.

FIGS. 2A and 2B show exterior views of LED light engine 100. As shown in FIGS. 2A, 2B, LED light engine 100 is a fully enclosed in a housing 200 having a small footprint suitable for bench top use. In an embodiment LED light engine 100 has dimensions of 110 mm×230 mm×190 mm (4.2 in×9.1 in×7.5 in). A three-sided cover 210 covers the top, left and right surfaces of LED light engine 100. The cover 210 includes vents 212 to allow cooling air to flow through the right side of the LED light engine 100. Adapter 108 is fitted to the front plate 214 of LED light engine 100. Back plate 220, includes a power switch 222, USB port 224, power connector 226 and foot pedal connector 228. LED light engine 100 sits on four feet 216 mounted to base plate 218. Housing 200 thus consists of three-sided cover 210, front plate 214, back plate 220, and base plate 218. Housing 200 protects the LED light engine 100 and substantially prevents the entry/exit of light, and air except as provided by vents through housing 200.

FIG. 2C shows a perspective view of LED light engine 100 with the three-sided cover 210 removed. As shown in FIG. 2C, a platform 230 is mounted vertically between front plate 214 and back plate 220. Platform 230 completely separates the left and right sides of the housing. The left side 232 of platform 230 is substantially planar for mounting and supporting the LED modules and optics. The right side 234 of platform 230 includes a large number of vertical fins 236 for cooling of platform 230. Platform 230 is preferably machined from aluminum or another conductive metal or metal alloy.

As shown in FIG. 2C, the interior of solid LED light engine 100 is divided by a platform 230. The left side 732 of platform 730 is substantially flat and supports the solid state light sources and associated optics. The right side 234 of platform 230 bears a plurality of fins 236 which provided a large surface area for the cooling of platform 230. The fins are arranged vertically parallel to the axis of the air flow rising from the bottom of the housing and escaping through the top of the housing. Platform 230, maintains the cooling air flow in the right portion of the housing between the platform 230 and the three-sided cover. This reduces the possibility of contamination of the optical components.

As shown in FIG. 2C, mounted to the left side 232 of platform 230 are three LED modules 241, 242, and 243 for generating light of selected wavelengths. Each of the LED modules 241, 242, and 243 includes a collimator 241c, 242c, and 243c which forms the light output from the module into a collimated beam. The light output of LED modules 241, 242, and 243 is combined into a single output beam using two dichroic mirrors 244, 245 which are also mounted to the left side 232 of platform 230. The single output beam of light is directed to output optics 256 which focuses the combined beam into a light guide (not shown) inserted in adapter 108.

In an embodiment of the invention, LED light engine 100 includes three LED modules 241, 242, and 243 each generating light of a different peak wavelength (color). The two dichroic mirrors serve 244, 245 color to create a single coaxial 3-color beam. In an embodiment the LED modules 241, 242, and 243 generate violet (405 nm), blue (440 nm), and cyan (485 nm) light. In a preferred embodiment, the output beam is substantially continuous over the spectrum of 380 nm-530 nm such that it is suitable for exciting a wide range of photoinitiators. Each individual LED light source is collimated so as to be efficiently combined by dichroic mirrors 244, 245 and after combination, the single coaxial beam is refocused by output optics 256 into a light guide for transport to the device or system to be illuminated. Additional or different colors can be used by replacing one or more of LED modules 241, 242, and 243. For example, UV light LED module including UV LEDS in place of or in addition to the violet LED module.

The cooling requirements for a solid state illumination system are substantially different than that for an incandescent light source. Incandescent lights typically release 90% or so of the heat they generate to their environment through radiation in the infrared and less than 10% through conduction. In comparison, LEDs typically release 90% or so of the heat they generate to their environment through conduction and less than 10% through conduction. Thermal dissipation is a key factor that limits the power output of an LED light source. Even though LEDs bulbs are considerably more efficient at converting electrical energy into light than incandescent light sources, but the LED components and the driver electronics can still create a considerable amount of heat. If this heat is not dissipated properly, the LED's quality of light, emission spectra, and life expectancy decrease dramatically. Thus, it is important in a solid state illumination system relying on LEDs to provide an effective solution for conductive cooling of the LEDs. Platform 230 provides both for mounting of LED modules 241, 242, and 243 as well as thermal regulation as described below.

As previously described cooling air is not circulated in the left portion of the housing. However, the LED modules 241, 242, and 243 generate heat during operation. This heat must be removed such that the temperature of the solid state light sources is maintained at a desired level. In prior devices, the individual solid state light sources were provided with individual finned heat sinks and air was passed over the heat sinks using a common or individual fan to remove heat—however, this cooling system allowed for the entry of dust and/or other contaminants into the light sources and onto the optical components. The dust and/or other contaminants could cause a number of problems including: reduction in optical efficiency, scattering of light within the housing, burning, and burning odor. In the LED light engine 100 shown in FIGS. 2A-2F, each of the LED modules 241, 242, and 243 is in good thermal contact with platform 230. The thermal contact is direct metal to metal contact or may be mediated by a thermal paste between the LED modules and the platform 230. Platform 230 is made from a conductive metal/metal alloy such that heat from the LED modules is rapidly conducted away towards fins 236 through which cooling air may circulate. Thus platform 230 serves both as an optical table for mounting and aligning the LED modules, dichroic mirrors and output optics as well as a common heat sink for the LED modules. The LED modules are suitably designed to efficiently transmit heat from their components to the platform 720 as described with respect to FIGS. 3A-3C below. LED modules are arranged on the platform 230 based upon their heat output for example in an embodiment, LED modules 241, 242, 243 each put out 25 watts of heat each. Thus, the thermal output of the light sources is considered when arranging the light sources to ensure that each is adequately cooled by the cooling airflow on the finned side of platform 230. Note, in FIG. 2E, for example that the LED modules 241, 242, 243 are arranged so as to be horizontally displaced from each other such that each is effectively cooled. In a preferred embodiment passive cooling of fins 236 by air passing through the vents in housing 200 (see FIGS. 2A, 2B) is sufficient to maintain the temperature of LED modules 241, 242, and 243 without the use of a fan. Note also that platform 230 divides the internal volume of housing 200 such that cooling air only flows through the right side over fins 236. The left side 230 of housing 200 is unvented such no external air passes around the optical components and LED modules 241, 242, and 243. This reduces the possibility of contamination by dust and the like.

FIGS. 2D and 2E show side views of LED light engine 100 with the three-side cover 210 removed. FIG. 2D shows the right side 234 of platform 230 showing fins 236 which are vertically mounted such that heated air can pass up through base plate 218 and out through vents 212 in three-sided cover 210 thus facilitating convective cooling of fins 236 without the use of a fan. A control board 240 is also housed adjacent the right side 234 of platform 230 and is connected to includes a power switch 222, USB port 224, power connector 226 and foot pedal connector 228 through back plate 220. Control board 240 also receives cooling air flow. Control board 240 includes the circuitry for driving the solid state light sources and sensors of LED light engine 100.

FIG. 2F shows a bottom view of LED light engine 100. Note that bottom plate 218 includes a plurality of slots 219 aligned with the gaps between fins 236 (not shown). Slots 219 are designed such that air can flow through slots 219 and between fins 236 thereby cooling platform 230 (not shown) by passive convection with requiring a fan.

The LED modules 241, 242, 243 are controlled by the controller board 240 either together or individually to control the spectral content of the output beam. In embodiments of the invention, three LED modules 241, 242, 243 produce spectral components centered on colors violet 405 nm, blue 425-460 nm, and cyan 460-500 nm. All the and three LED modules 241, 242, 243 can be turned on at the same time such that the different colors are combined to create a substantially continuous spectrum over the range 380 nm-530 nm.

FIG. 2G illustrates a control system of the LED light engine 100. As shown in FIG. 2G, control board 240 includes a controller 270. Controller 270 includes an input/output system 272 for receiving data from the various sensors, input port and input devices and sending data to the data output port and or any indicator/display devices. Controller 270 is coupled to power output system 274 which provides power to the electrical, optical and mechanical components of LED light engine 100. Because of the solid state nature and independently operable designs of the light sources, coupled to fast (approximately 10 ns) decay times of typical materials employed, the solid state illumination system does not require a mechanical shutter and is capable of rise times of less than 20 μs and fall times of less than 2 μs under the control of controller 270 which is compatible with triggering by a control device 104 connected to USB port 224 and/or by a foot pedal connected to foot-pedal port 228. Each light source is operated simultaneously to generate a continuous light output spectrum. Alternatively, each source can be switched independently to generate an output of the desired spectral power distribution and/or color.

In the control system embodiment shown in FIG. 2G, controller 270 is coupled by input/output system 272 to USB port 224, foot pedal input 228, safety flap sensor 276, toggle switch 222, additional sensor(s) 278, display/indicators 280, as well as the heat and light sensors of LED modules 241, 242, 243. Controller 270 is coupled to power output system 274 which provides electrical power to drive the LEDs and laser diodes of LED modules 241, 242, 243. Additional sensors 278, display/indicators 280 and inputs/switches and outputs may be added to LED light engine 100 as necessary to support desired functionality for the system, however, typically a control device 104 connected to USB port 224 is used to control and monitor LED light engine 100 and provides control and data display flexibility through a software application. For example, as shown in FIG. 1A a control device 104, in the form of a touchscreen tablet running software which allows the control device 104 to control operation of LED light engine 100. The touchscreen tablet, enables the user to: set intensity for each LED module separately or as a group; set and initiate a countdown timer; and program custom curing cycles. Initiation of such programmed outputs can be actuated by the touchscreen or a foot-pedal (not shown). Control device 104 is connected to LED light engine 100 by USB cable 106, however, in alternative embodiments, a wireless or network connection can be used (Bluetooth, Wifi, NFC, Ethernet etc).

LED Module For Photocuring System

Figure 3A:
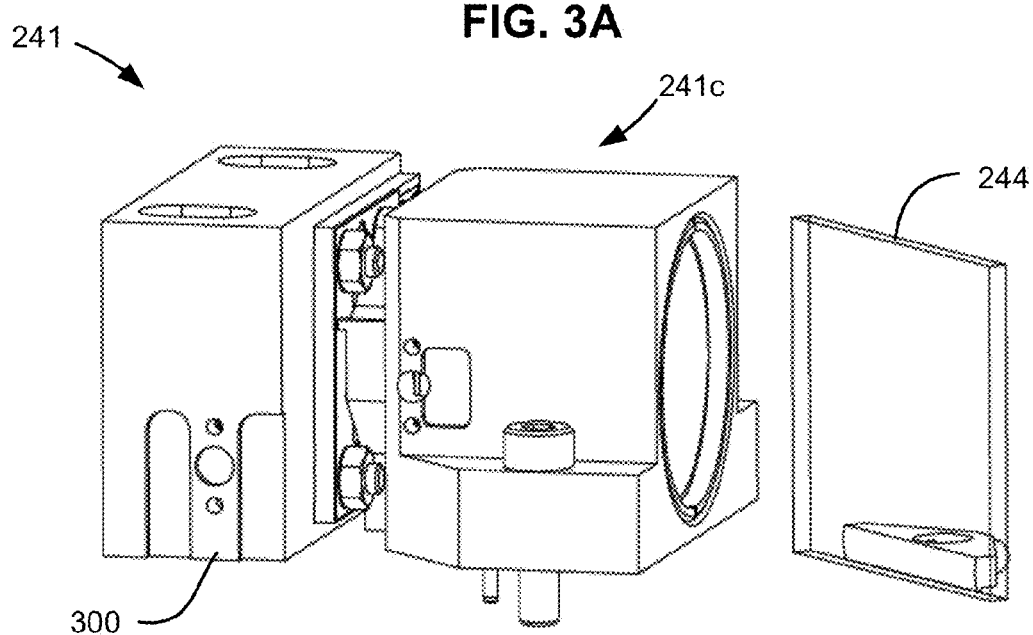
FIG. 3A shows a perspective view of a LED module of the LED Light Engine of FIGS. 2A & 2B according to an embodiment of the invention.
Figure 3B:
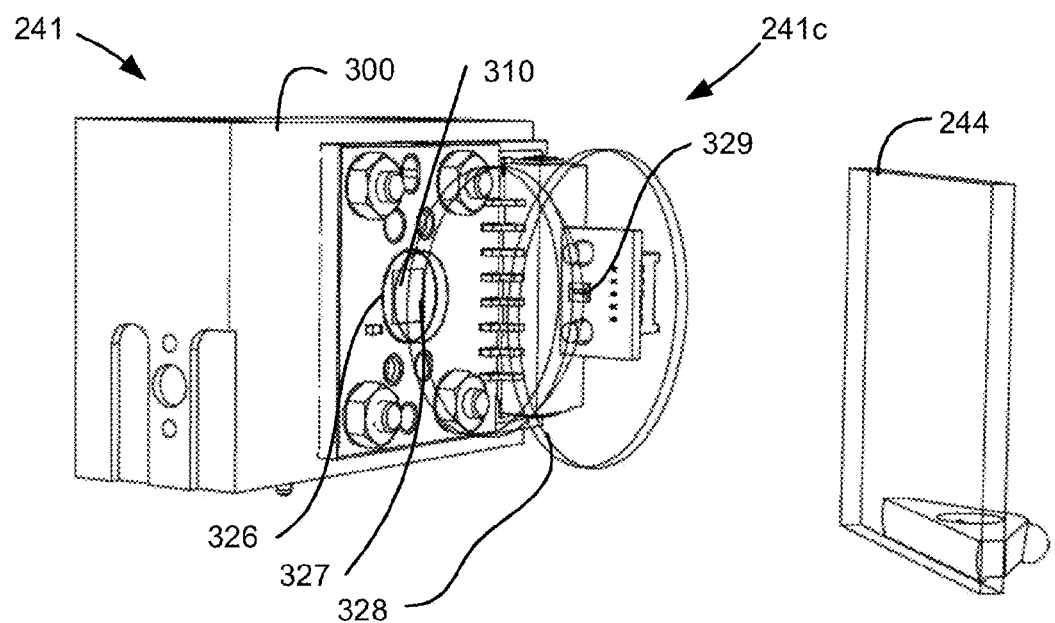
FIG. 3B shows a partial perspective view of the LED module of FIG. 3A.

FIGS. 3A-3C shows views of LED module 241 and collimator 241c. LED modules 242 and 243 have the same design though each of LED modules 241, 242 and 243 preferably includes LEDs which emit light of different wavelengths than the others of LED modules 241, 242 and 243. FIG. 3A shows a perspective view of LED module 241, collimator 241c and associated dichroic mirror 244. As shown in FIG. 3A, LED module 241 includes a base 300 adapted to be mounted to platform 230 (see FIGS. 7C-7E). Collimator 241c is mounted to base 300.

FIG. 3B shows a partial perspective view of LED module 241, collimator 241c and associated dichroic mirror 244. As shown in FIG. 3B, LED module 241 includes an LED die 310. LED die 310 includes a plurality of light-emitting diodes on the same substrate. The substrate is mounted in direct or indirect thermal contact with base 300 such that heat generated by the light-emitting diodes during operation is transmitted to base 300. Base 300 is secured in thermal contact with platform 230 such that heat is rapidly transferred to platform 230 and then dissipated from fins 236.

Referring again to FIG. 3B, light emitted from LED die 310 is collected through plano-convex-lens 326 placed over die 310. The light passes through plano-convex lens 326 and is collimated by plano-convex lenses 327, 328 of collimator 241c. A light sensor 329 is placed adjacent plano-convex lens 327 where it receives scattered light in order to monitor the light output of LED die 310. After passing plano-convex lenses 327, 328 the collimated light beam is directed at dichroic mirror 244. Dichroic mirror 244 is aligned such that the collimated beam of light is directed along an optical axis towards output optics 256 (see FIG. 2E).

FIG. 3C shows a sectional view of LED module 241 and collimator 241c. As shown in FIG. 3C, LED module 241 includes an LED die 310. LED die 310 includes a plurality of light-emitting diodes on the same substrate. The substrate is mounted in direct or indirect thermal contact with base 300 such that heat generated by the light-emitting diodes of LED die 310 during operation is transmitted to base 300. Base 300 is secured in thermal contact with platform 230 such that heat is rapidly transferred to platform 230 and then dissipated from fins 236 (not shown, but see FIG. 2D). Referring again to FIG. 3C, light emitted from LED die 310 is collected through plano-convex-lens 326 placed over die 310. The light passes through plano-convex lens 326 and is collimated by plano-convex lenses 327, 328 of collimator 241c.

Output Optics for Photocuring System

Figure 4C:
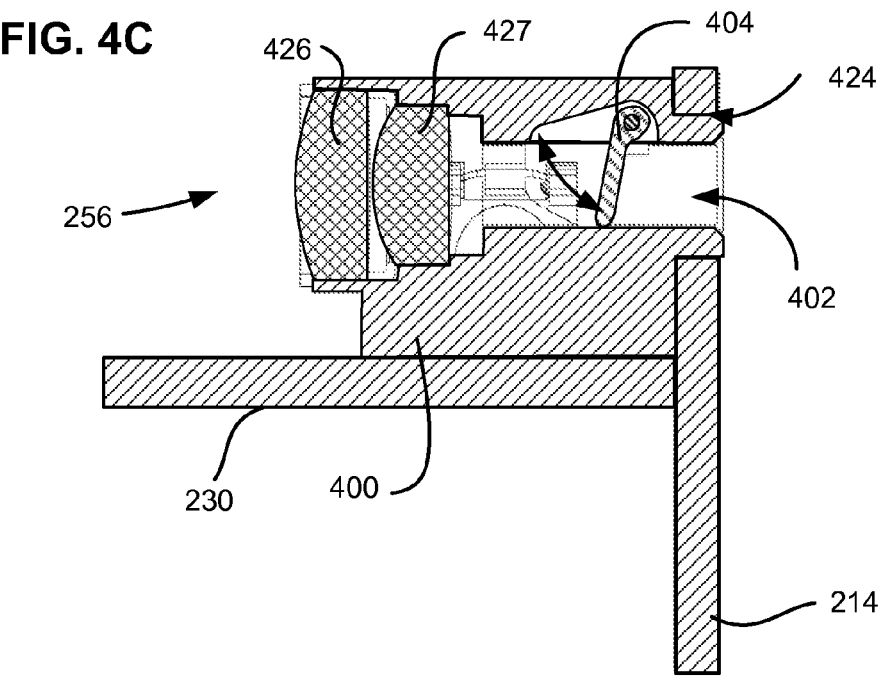
FIGS. 4C and 4D show different sectional views of the output optics subsystem of FIG. 4A.

FIGS. 4A-4D illustrate output optics 256 of LED light engine 100 (see FIGS. 2C and 2E). As shown in FIG. 4A, output optics 256 receives the collimated combined beam of light 254 from all the light sources of LED light engine 100, focuses the combined beam 254 and directs it into the aperture 428 of light guide 102. An adapter 108 connects light guide 102 to output optics 256 and positions light guide 102 such that the aperture 428 of the light guide is correctly positioned to receive the focused combined beam of light 254. Output optics 256 are positioned against front plate 214 such that light guide 102 can be connected to output optics 256 through an aperture in front plate 214.

As shown in FIG. 4B, output optics 256 includes two plano-convex lenses 426, 427. Plano-convex lenses 426, 427 receive the collimated combined beam of light 254 from all the light sources of LED light engine 100, focuses the combined beam 254 and directs it into the aperture 428 of light guide 102. Light guide 102 transmits the combined beam to a location or instrument used to excite a photoinitiator.

Figure 4D:
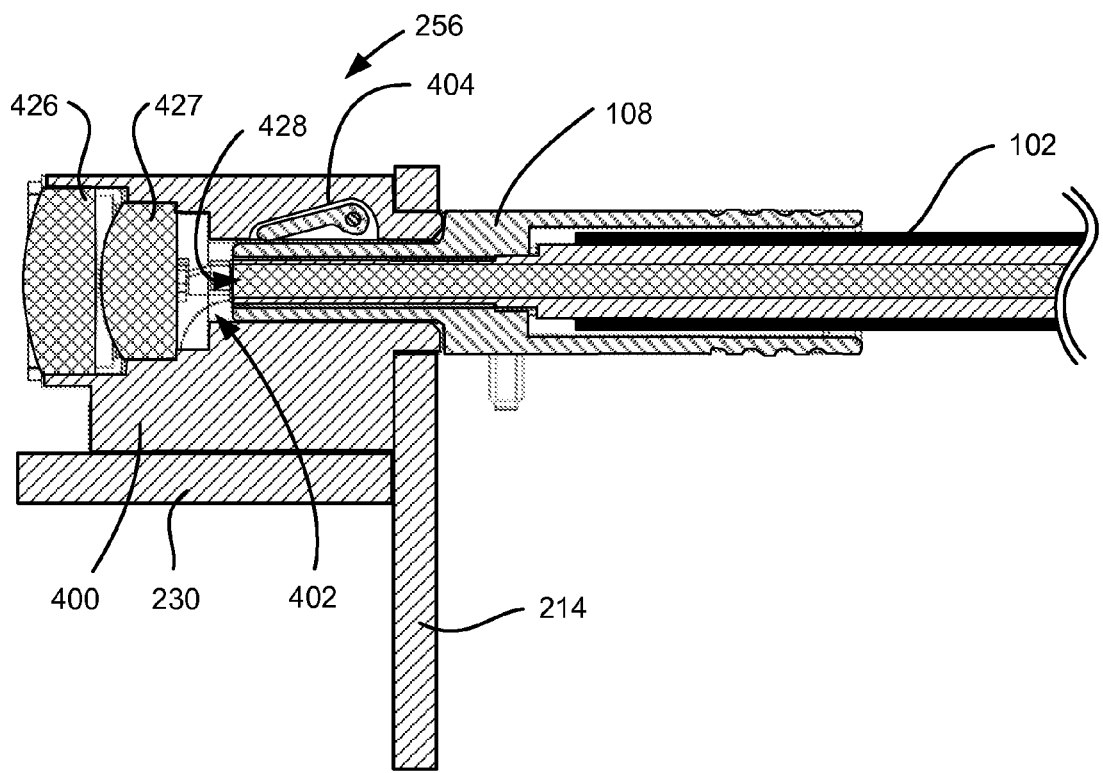

FIGS. 4C and 4D are sectional views of output optics 256 illustrating attachment of a light guide 102. FIG. 4C shows output optics without light guide 102 in place. As shown in FIG. 4C, light guide 102 includes a housing 400 which defines a lumen 402. Housing 400 is mounted to platform 230. Housing 400 projects through aperture 424 in front plate 214 such that lumen 402 is accessible from the exterior of solid state illumination system 700. As shown in FIG. 4C, a safety flap 404 occludes lumen 402 to prevent the exit of light or entry of contaminants through lumen 402 when light guide 102 is not connected. Safety flap 404 is spring loaded such that it occludes lumen 402 automatically upon removal of a light guide 102. Safety flap 404 pivots out of the way when a light guide 102 is inserted. One or more limit sensors (not shown) are coupled to safety flap 404 to sense the position of safety flap 404 (and thus the presence or absence of a light guide) and provide such information to controller board 240. The safety flap 404 and sensor operate as dual interlock system to prevent light output from LED light engine 100 both mechanically and electronically when the light guide 102 is removed.

As shown in FIG. 4D, light guide 102 is received in an adapter 108 which connects light guide 102 to output optics 256 and positions light guide 102 such that the aperture 428 of the light guide 102 is correctly positioned to receive the focused combined beam of light 254. When adapter 108 and light guide 102 are inserted into lumen 402 of housing 400, safety flap 404 pivots out of the way. Aperture 428 is positioned coaxial with plano-convex lenses 426, 427 such that the combined beam of light 254 is focused into aperture 428 of light guide 102. Light guide 102 transmits the combined beam to a location or instrument used to excite a photoinitiator.

The foregoing description of the various embodiments of the present invention has been provided for the purposes of illustration and description. It is not intended to be exhaustive or to limit the invention to the precise forms disclosed. Many modifications and variations will be apparent to the practitioner skilled in the art. Embodiments were chosen and described in order to best describe the principles of the invention and its practical application, thereby enabling others skilled in the art to understand the invention, the various embodiments and with various modifications that are suited to the particular use contemplated. Other features, aspects and objects of the invention can be obtained from a review of the figures and the claims. It is to be understood that other embodiments of the invention can be developed and fall within the spirit and scope of the invention and claims.

What is claimed is:
1. A photocuring system comprising:
a housing enclosing a space;
a metal platform having a first substantially planar surface and a second surface;
the metal platform vertically dividing the enclosed space into a first volume defined by the first substantially planar surface and the housing, and a second volume defined by the second surface and the housing;
the metal platform having on the second surface a plurality of vertically oriented fins;
a first light source positioned within said first volume, the first light source having a first solid state light source, a collimator, and a first metal base, wherein the first solid state light source emits light of a first wavelength which is received by the collimator which generates a collimated first light beam;
a second light source positioned within said first volume, the second light source having a second solid state light source, a collimator, and a second metal base, wherein the second solid state light source emits light of a second wavelength which is received by the collimator which generates a collimated second light beam;
a third light source positioned within said first volume, the third light source having a third solid state light source, a collimator, and a third metal base, wherein the third solid state light source emits light of a third wavelength which is received by the collimator which generates a collimated third light beam;
a plurality of dichroic elements positioned in said first volume and mounted to said first substantially planar surface of said metal platform wherein the plurality of dichroic elements combine the collimated first light beam, collimated second light beam, and collimated third light beam into a combined light beam; and
an output optical stage, positioned in said first volume and mounted to said first substantially planar surface of said metal platform, the optical stage including a lumen for receiving a light guide and comprising a plurality of lenses positioned to receive the combined light beam and focus the combined light beam into an output beam of light suitable for illuminating the light guide;
wherein said first metal base is mounted to said first substantially planar surface of said metal platform such that it provides a heat conducting path between said first solid state light source and the metal platform through which heat generated by the first solid state light source is conducted to the metal platform;

wherein said second metal base is mounted to said first substantially planar surface of said metal platform such that it provides a heat conducting path between said second solid state light source and the metal platform through which heat generated by the second solid state light source is conducted to the metal platform;

wherein said third metal base is mounted to said first substantially planar surface of said metal platform such that it provides a heat conducting path between said third solid state light source and the metal platform through which heat generated by the third solid state light source is conducted to the metal platform;

wherein the housing has a top vent into said second volume and a bottom vent into said second volume whereby hot air can escape from the second volume through the top vent and cool air can be drawn into the second volume through the bottom vent to provide air flow through the second volume and between said vertically oriented fins to provide passive convective cooling of the metal platform and wherein the housing substantially seals the first volume to prevent contamination.

2. The photocuring system of claim 1, further comprising:
a control board mounted within the second volume of the housing, the control board provides current to said plurality of light sources; and
a touchscreen control device external to said housing;
wherein the touchscreen control device is coupled to said control board and configured to control operation of said first light source, second light source and third light source.

3. The photocuring system of claim 2, wherein said output optical stage, includes a spring-loaded mechanical flap within said housing that automatically obstructs said lumen of the output optical stage in the absence of a light guide.

4. The photocuring system of claim 3, in combination with a light guide coupled to the output optical stage through an aperture in said housing, the light guide transmits the output beam of light from the photocuring system.

5. The photocuring system of claim 1, further comprising a control board mounted within the second volume of the housing, the control board provides current to said first solid state light source, second solid state light source, and third solid state light source.

6. The photocuring system of claim 1, wherein said output beam of light has an intensity of at least 10 W/cm$^2$ when used with a 3 mm diameter light guide.

7. The photocuring system of claim 1, wherein said output beam of light has a spectral content which is substantially continuous between 380 nm and 530 nm.

8. A photocuring system comprising:
a housing having a top surface and a bottom surface and enclosing a space;
a metal platform having a first substantially planar surface and a second surface;
the metal platform dividing the enclosed space into a first volume defined by the first substantially planar surface and the housing, and a second volume defined by the second surface and the housing;
the metal platform having on the second surface a plurality of vertically oriented fins;
a first light source positioned within said first volume, the first light source having a first LED module, a collimator, and a first metal base, wherein the first LED module emits violet light which is received by the collimator which generates a collimated violet light beam;
a second light source positioned within said first volume, the second light source having a second LED module, a collimator, and a second metal base, wherein the second LED module emits blue light which is received by the collimator which generates a collimated blue light beam;
a third light source positioned within said first volume, the third light source having a third LED module, a collimator, and a third metal base, wherein the third LED module emits cyan light which is received by the collimator which generates a collimated cyan light beam;
a plurality of dichroic elements positioned in said first volume and mounted to said first substantially planar surface of said metal platform wherein the plurality of dichroic elements combine the collimated violet light beam, collimated blue light beam, and collimated cyan light beam into a combined light beam; and
an output optical stage, positioned in said first volume and mounted to said first substantially planar surface of said metal platform, the optical output stage comprising a lumen for receiving a light guide and a plurality of lenses configured to receive the combined light beam and focus the combined light beam into an output beam of light suitable for transmission into the light guide;
wherein said first metal base is mounted to said first substantially planar surface of said metal platform such that it provides a heat conducting path between said first solid state light source and the metal platform through which heat generated by the first solid state light source is conducted to the metal platform;
wherein said second metal base is mounted to said first substantially planar surface of said metal platform such that it provides a heat conducting path between said second solid state light source and the metal platform through which heat generated by the second solid state light source is conducted to the metal platform;
wherein said third metal base is mounted to said first substantially planar surface of said metal platform such that it provides a heat conducting path between said third solid state light source and the metal platform through which heat generated by the third solid state light source is conducted to the metal platform;
wherein the housing has a top vent through said top surface into said second volume and a bottom vent through said bottom surface into said second volume whereby air can escape from the second volume through the top vent and air can be drawn into the second volume through the bottom vent to provide air flow through the second volume and between said vertically oriented fins to provide passive convective cooling of the metal platform and wherein the housing substantially seals the first volume to prevent contamination.

9. The photocuring system of claim 8, further comprising:
a control board mounted within the second volume of the housing, wherein the control board provides current to said first LED module, second LED module, and third LED module; and
a touchscreen control device external to said housing;
wherein the touchscreen control device is coupled to said control board and configured to control operation of said first LED module, second LED module and third LED module.

10. The photocuring system of claim 8 wherein said output optical stage includes a spring-loaded mechanical flap which automatically obstructs said lumen of the output optical stage unless a light guide is connected to the output optical stage.

11. The photocuring system of claim 8, in combination with a light guide coupled through an aperture in said housing to said output optical stage.

12. The photocuring system of claim 8 comprising:
wherein the output beam is substantially continuous between 380 nm and 530 nm and has an intensity of at least 10 W/cm² when used with a 3 mm diameter light guide.

13. The photocuring system of claim 8 further comprising:
a control board mounted within the second volume of the housing, wherein the control board provides current to said first LED module, second LED module, and third LED module; and
a foot pedal external to said housing but coupled to said control board wherein the foot pedal is configured to control light output by the photocuring system.

14. The photocuring system of claim 8 further comprising:
a control board mounted within the second volume of the housing, wherein the control board provides current to said first LED module, second LED module, and third LED module; and
an electronic sensor in said optical output stage, wherein the electronic sensor is coupled to said control board and operative to turn off said first LED module, second LED module, and third LED module unless a light guide is connected to the optical output stage; and
a mechanical flap which automatically obstruct said lumen of the output optical stage unless a light guide is connected to the optical output stage.

\* \* \* \* \*